United States Patent [19]
Seifert et al.
[11] Patent Number: 4,737,596
[45] Date of Patent: Apr. 12, 1988

[54] HYBRID CORN PLANT AND SEED

[75] Inventors: Robert Seifert, Des Moines; Stephen W. Noble, Johnston, both of Iowa; William S. Niebur, Princeton, Ill.

[73] Assignee: Pioneer Hi-Bred International, Inc., Johnston, Iowa

[21] Appl. No.: 8,376

[22] Filed: Jan. 29, 1987

[51] Int. Cl.[4] .......... A01H 1/02
[52] U.S. Cl. .......... 800/1; 47/58; 47/DIG. 1
[58] Field of Search .......... 47/58, DIG. 1; 800/1

*Primary Examiner*—Robert E. Bagwill
*Attorney, Agent, or Firm*—Saidman, Sterne, Kessler & Goldstein

[57] ABSTRACT

According to the invention, there is provided a hybrid corn plant, designated 3471, produced by crossing two Pioneer Hi-Bred International, Inc. proprietary inbred corn lines. This invention thus relates to the hybrid seed 3471, the hybrid plant produced from the seed, and variants, mutants, and modifications of Pioneer hybrid 3471. This hybrid corn plant is characterized by superior qualities of good ear size, excellent late-season plant health and seedling (young plant) vigor, and fast dry-down in the field. 3471 is relatively tall and flowers late for its relative maturity classification.

6 Claims, No Drawings

HYBRID CORN PLANT AND SEED

FIELD OF THE INVENTION

This invention is in the field of plant breeding, specifically hybrid corn breeding.

BACKGROUND OF THE INVENTION

The goal of plant breeding is to combine in a single variety/hybrid various desirable traits of the parental lines. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous plants from differing backgrounds or two homozygous lines produce a uniform population of hybrid plants that may be heterozygous for many gene loci. A cross of two plants each heterozygous at a number of gene loci will produce a population of hybrid plants that differ genetically and will not be uniform.

Corn plants (*Zea mays* L.) can be bred by both self-pollination and cross-pollination techniques. Corn has male flowers, located on the tassel, and female flowers, located on the ear, on the same plant. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced. $F_1 \rightarrow F_2$; $F_2 \rightarrow F_3$; $F_3 \rightarrow F_4$; $F_4 \rightarrow F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A hybrid corn variety is the cross of two inbred lines, each of which may have one or more desirable characteristics lacked by the other or which complement the other. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

The development of a hybrid corn variety involves three steps: (1) the selection of superior plants from various germplasm pools; (2) the selfing of the superior plants for several generations to produce a series of inbred lines, which although different from each other, each breed true and are highly uniform; and (3) crossing the selected inbred lines with unrelated inbred lines to produce the hybrid progeny ($F_1$). During the inbreeding process the vigor of the lines decreases. Vigor is restored when two unrelated inbred lines are crossed to produce the hybrid progeny ($F_1$). An important consequence of the homozygosity and homogeniety of the inbred lines is that the hybrid between any two inbreds will always be the same. Once the inbreds that give the best hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid, is produced from four inbred lines crossed in pairs ($A \times B$ and $C \times D$) and then the two $F_1$ hybrids are crossed again $(A \times B) \times (C \times D)$. Much of the hybrid vigor exhibited by $F_1$ hybrids is lost in the next generation ($F_2$). Consequently, seed from hybrid varieties is not used for planting stock.

Hybrid corn seed can be produced by manual detasseling. Alternative strips of two inbred varieties of corn are planted in a field, and the pollen-bearing tassels are removed from one of the inbreds. Providing that there is sufficient isolation from sources of foreign corn pollen, the ears of the detasselled inbred (female) will be fertilized only from pollen from the other inbred (male), and the resulting seed is therefore hybrid and will form hybrid plants.

The laborious detasseling process can be avoided by using cytoplasmic male-sterile (CMS) inbreds. Plants of a CMS inbred are fertilized with pollen from another inbred that is not male-sterile. Pollen from the second inbred can contribute genes that make the hybrid plants male-fertile. Usually seed from detasseled normal corn and CMS produced seed of the same hybrid is blended to insure that adequate pollen loads are available for fertilization when the hybrid plants are grown.

Corn is an important and valuable field crop. Thus, a continuing goal of plant breeders is to develop stable high yielding corn hybrids that are agronomically sound. The reasons for this goal are obvious: to maximize the amount of grain produced on the land used and to supply food for both animals and humans.

SUMMARY OF THE INVENTION

According to the invention, there is provided a hybrid corn plant, designated 3471, produced by crossing two Pioneer Hi-Bred International, Inc. proprietary inbred corn lines. This invention thus relates to the hybrid seed 3471, the hybrid plant produced from the seed, and variants, mutants, and modifications of hybrid 3471. This hybrid corn plant is characterized by superior qualities of good ear size, excellent late-season plant health and seedling (young plant) vigor, and fast dry-down in the field. 3471 is relatively tall and flowers late for its relative maturity classification.

DEFINITIONS

In the description and examples that follow, a number of terms are used herein. In order to provide a clear and consistent understanding of the specification and claims, including the scope to be given such terms, the following definitions are provided:

Predicted RM. This trait, predicted relative maturity (RM), for a hybrid is based on the harvest moisture of the grain. The relative maturity rating is based on a known set of checks and utilizes standard linear regression analyses.

GDU Shed. The GDU shed is the number of growing degree units (GDU) required for an inbred line or hybrid to shed pollen from the time of planting. Growing degree units are calculated by the Barger Method, where the heat units for a 24-hour period are:

$$GDU = \frac{(\text{Max.} + \text{Min.})}{2} - 50.$$

The highest maximum used is 86° F. and the lowest minimum used is 50° F. For each hybrid it takes a certain number of GDU's to reach various stages of plant development. GDU's are a way of measuring plant maturity.

MN RM. This represents the Minnesota Relative Maturity Rating (MN RM) for the hybrid and is based on the harvest moisture of the grain relative to a standard set of checks of previously determined MN RM rating. Regression analyses is used to compute this rating.

BL RM. This is a relative maturity rating based on GDU's required for the hybrid to reach black layer (physiological maturity). Regression analyses is used to compare the given hybrid to a standard set of checks.

GDU BL. This is the number of growing degree units required for the hybrid to reach black layer from the time that it was planted.

SLK RM. This is the relative maturity based on the number of GDU's to silking of a hybrid relative to a standard set of checks of predetermined SLK RM. Regression analyses is used to compute this relative rating.

GDU Slk. This is the number of GDU's that the hybrid requires to reach silking from the time of planting.

Selection Index. The selection index gives a single measure of the hybrid's worth based on information for up to five traits. A corn breeder may utilize his or her own set of traits for the selection index. One of the traits that is almost always included is yield. The selection index data presented in the tables in the specification represent the mean value averaged across testing stations.

Yield (Bushels/Acre). The yield in bushels/acre is the actual yield of the grain at harvest adjusted to 15.5% moisture.

Percent Yield. The percent yield is the yield obtained for the hybrid in terms of percent of the mean for the experiments in which it was grown.

Moisture. The moisture is the actual percentage moisture of the grain at harvest.

Yield/Moisture. This represents a rating for a hybrid's yield relative to its grain moisture at harvest.

Dry Down. This represents the relative rate at which a hybrid will reach acceptable harvest moisture compared to other hybrids. A high score indicates a hybrid that dries relatively fast while a low score indicates a hybrid that dries slowly.

Drought Tolerance. This represents a rating for drought tolerance, and is based on data obtained under stress conditions.

Stalk Lodging. This is the percentage of plants that do not stalk lodge, i.e. stalk breakage, as measured by either natural lodging or pushing the stalks over and determining the percentage of plants that broke off below the ear. This is a relative rating of a hybrid to other hybrids for standability.

Root Lodging. The root lodging is the percentage of plants that do not root lodge, i.e. those that lean from the verticle axis at an approximate 30° angle or greater would be counted as root lodged.

Plants Per Acre: This is the plant density estimated for the hybrid on a per acre basis.

Ears Per Plot. This is the measure of the number of ears per plot adjusted for stand and given as the percentage.

Stay Green. Stay green is the measure of plant health near the time of black layer formation (physiological maturity). A high score indicates better late-season plant health.

Test Weight. This is the measure of the weight of the grain in pounds for a given volume (bushel) adjusted for percent moisture.

Cob Score. The cob score is a rating of how well the grain is shelled off the cob and how badly the cob is broken up going through the combine. A high score indicates that the grain shells off of the cob well and the cob does not break.

Purple Seedling. This is an indication of purple coloring at the seedling stage. A low score indicates greater purple coloring.

Grain Quality. This is a rating for the general quality of the shelled grain as it is harvested based on the color of the harvested grain, any mold on the grain, and any cracked grain. High scores indicate good grain quality.

Seedling Vigor. This is the visual rating of the amount of vegetative growth after emergence at the seedling stage (approximately five leaves). A higher score indicates better vigor.

Early Stand Count. This is a measure of the stand establishment in the spring, and represents the number of plants that emerge on a per plot basis for the hybrid.

Plant Height. This is a measure of the height of the hybrid from the ground to the tip of the tassel and is measured in six inch increments.

Ear Height. The ear height is a measure from the ground to the ear node attachment and is measured in six inch increments.

Dropped Ears. This is a measure of the percentage of plants that did not drop ears prior to harvest.

Brittle Stalks. This is a measure of the stalk breakage near the time of pollination of the hybrids, and is an indication of whether a hybrid would snap or break at the time of flowering under severe winds. Data are presented as percentage of plants that did not snap.

DETAILED DESCRIPTION OF THE INVENTION

Hybrid 3471 is a single cross made with the Pioneer Hi-Bred proprietary corn inbred lines PH86471A and PH86471B.

To produce 3471, either inbred parental line can be used as the female parent or the male parent. Preferably inbred PB86471A should be the female of the cross and inbred PH86471B should be the male of the cross. Production planting should be timed so that the male pollen is shed at the same time that the female silks are receptive to the pollen. The male inbred PH86471B sheds pollen 120 GDU's earlier than the female PH86471A silks. Therefore the planting of the male inbred should be delayed 120 GDU's to obtain optimum pollination with the female inbred. The hybrid corn seed 3471 produced by this cross can then be planted to produce the hybrid plant.

3471 is a fast drying single cross with an excellent record for stalk quality. It is very tall and high eared with long shanks, good ear attachment, good ear size, and excellent stay green (late season plant health). In spite of the tall plant structure, its root lodging resistance is above average. Data suggest that this hybrid will perform best south of its adapted maturity zone and east of Nebraska. The hybrid is good for stand establishment and seedling vigor. It demonstrates exceptionally fast growth from the five leaf stage until flowering. Because of healthy stalks and good European corn borer (second brood) tolerance, plant tops do not break out of 3471 until late in the growing season, which accentuates its tall plant stature.

3471 is characterized by having good yield, excellent standability, good late season plant health, good early season vigor, and fast drydown. It also has above average tolerance to corn lethal necrosis, Helminthosporium leaf blight and second generation European corn borer infestation. The hybrid is tall with high ear placement. 3471 has 119 RM rating for both maturity to silk and maturity to black layer but is 114 RM based on harvest moisture.

This hybrid has the following characteristics based on descriptive data collected at Johnston, Iowa:

A. Maturity

Growing degree units to 50% of plants in silk: 1459
Growing degree units of physiological maturity: 2757
Minnesota relative maturity in days: 114

B. Plant

Height (to tassel tip): 307 cm
Ear height (to base of top ear): 122 cm
Length of top internode: 15 cm
Number of tillers: None
Number of ears per stalk: One
Cytoplasm type: Normal

C. Leaf

Color: Medium green (WF9)
Angle from stalk: <30°
Sheath pubescence: Light (W22)
Marginal waves: Hy
Longitudinal creases: Many (PA11)
Number of leaves per mature plant: 21
Length of ear node leaf: 98 cm

D. Tassel

Number of lateral branches: 12
Branch angle from central spike: >45°
Peduncle length (from top leaf to basal branches): 30 cm
Pollen shed: Heavy (KY21)
Anther color: Green
Glume color: Green

E. Ear (husked ear data unless stated otherwise):

Length: 21 cm
Mid-point diameter: 44 mm
Weight: 228 g
Kernel rows: 16; distinct; straight
Silk color (exposed at silking stage): Green
Husk color: Fresh/light green; dry/buff
Husk extension (harvest stage): Short (tip of ear exposed)
Shank: 22 cm long; internodes: 8
Taper: Slight
Position at dry husk stage: Upright
Drying time (unhusked ear): Fast

F. Kernel (dried)

Size (from ear mid-point): 13 mm long; 8 mm wide; 5 mm thick
Shape grade (% rounds): <20
Pericarp color: Colorless
Aleurone color: Homozygous; yellow
Endosperm color: Yellow
Endosperm type: Normal starch
Weight/100 seeds (unsized samples): 36.4 g

G. Cob

Diameter at mid-point: 24 mm
Strength: strong
Color: Red

H. Disease Resistance

Corn lethal necrosis: Tolerant
MDMV Complex: Intermediate
Anthracnose stalk rot: Intermediate
Southern leaf blight: Intermediate
Northern leaf blight: Intermediate
H. carbonum leaf blight: Tolerant
Common rust: Tolerant
Gray leaf spot: Susceptible
Goss' bacterial wilt: Susceptible
Common smut: Tolerant
Head smut: Susceptible
Downy mildew: Susceptible
Fusarium ear rot: Susceptible

I. Insect Resistance

European corn borer 1 leaf feeding: Intermediate
European corn borer 2: Tolerant
Corn root worm root lodging: Tolerant This invention includes the hybrid corn seed of 3471, the hybrid corn plant produced from the hybrid corn seed, and variants, mutants, and modifications of 3471. This invention also relates to the use of 3471 in producing three-way and double crosses hybrids.

The terms variant, modification, and mutant refer to a hybrid seed or a plant produced by that hybrid seed which is phenotypically similar to 3471.

As used herein, the term "plant" includes plant cells, plant protoplasts, plant cell or tissue culture from which corn plants can be regenerated, plant calli, plant clumps and plant cells that are intact in plants or parts of plants, such as flowers, kernels, ears, cobs, leaves, husks, stalks and the like.

Tissue culture of corn is described in European Patent Application No., publication number 160,390, incorporated herein by reference. Corn tissue culture procedures are also described in Green and Rhodes, "Plant Regeneration In Tissue Culture of Maize," *Maize for Biological Research,* (Plant Molecular Biology Association, Charlottesville, Va. 1982) at 367-372.

USES OF CORN

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide starch, syrups, and dextrose for food use. Corn oil is recovered from corn germ, which is a by-product of both dry- and wet-milling industries.

Corn is also used extensively as livestock feed primarily to beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel, to make charcoal.

The seed of 3471, the hybrid corn plant produced from the seed, and various parts of the hybrid corn plant can be utilized for human food, livestock feed, and as a raw material in industry.

EXAMPLES

In the examples that follow, the traits and characteristics of 3471 are given. The history of this hybrid is as follows: The hybrid was first made at the Pioneer Hi-Bred International, Inc., Johnston, Iowa Research Station. The hybrid was tested by the Johnston station in preliminary first year trials. Based on the record of 3471 in the preliminary trial, it was submitted as a wide area nomination for additional, second year testing.

In the second year, the hybrid 3471 was tested in elite research trials by the Johnston, Iowa and Princeton, Ill. Corn Research Stations. It was also tested at the Johnston Corn Research Station in a preliminary hybrid test. In the second year testing, there were 3,933 non-specialty hybrids evaluated. Of these 3,933 hybrids, 374 were wide area hybrids. A total of 36 replications or "reps" (one experiment/one location/one time) of data were collected on the hybrid 3471 for some traits in the elite trials.

In the second year testing, the hybrid seed of 3471 was produced for the following research stations: Algona, Iowa; Bowling Green, Ohio; Carrollton, Mo.; Johnston, Iowa; Marion, Iowa; North Platte, Nebr.; Princeton, Ill.; Shelbyville, Ill.; Windfall, Ind.; Princeton, Ind.; and York, Nebr. The hybrid seed 3471 was produced at winter nursery sites (Homestead, Fla. and Hekaha, Kauai, Hawaii) for some of the stations given. The rest of the seed was produced by some of the stations given in their summer nurseries.

In the third year trials, the hybrid 3471 was tested widely in advanced research trials and 293 replications of data were collected on some traits.

In the fourth year trials, the hybrid of 3471 was tested widely in advanced research trials. Up to 498 replications of data were collected in elite research trials for some traits. Also this hybrid was strip-tested widely by the various Pioneer marketing divisions in its adapted maturity zone across the United States. In conjunction with the yield testing, this hybrid was evaluated in disease and insect tests to determine its tolerance to various pests relative to other Pioneer hybrids. Limited data were collected at Johnston, Iowa, to ascertain its relative herbicide tolerance compared to other Pioneer hybrids.

Hybrid seed 3471 has been deposited at the American Type Culture Collection (ATCC) depository on Dec. 30, 1986, and designated ATCC number 40301.

In the examples that follow, the data collected on corn hybrid 3471 is presented for the key characteristics and traits. The scores are on a scale of 1 to 9, with 9 being the best unless otherwise indicated. The scores based on extensive testing are subjective in nature, but include input from expert corn researchers.

EXAMPLE I

Comparison of Various Corn Hybrid Characteristics

Comparison of the characteristics of 3471 were made against Pioneer brand hybrid 3475, a corn hybrid marketed in the same maturity zone as 3471.

Comparison of the characteristics of 3471 was also made against DeKalb Pfizer's T1100 corn hybrid. The results of these comparisons are given in Tables IA and Tables IB and represent research results that were collected over three years.

TABLE IA

COMPARISON OF HYBRIDS 3471 AND 3475 FROM PERIOD OF YEARS RESEARCH DATA

| HYBRID | PREDICTED RM | SELECTION INDEX | PERCENT YIELD | YIELD (BU./AC.) | MOISTURE | GDU SHED | STALK LODGING | ROOT LODGING | EARS/PLOT | STAY GREEN |
|---|---|---|---|---|---|---|---|---|---|---|
| No. of Reps | 705 | 705 | 696 | 696 | 708 | 167 | 684 | 280 | 271 | 421 |
| 3471 | 114 | 105 | 104 | 151.8 | 21.2 | 1404 | 98.0 | 94.9 | 92.8 | 6.6 |
| 3475 | 114 | 100 | 102 | 148.7 | 21.2 | 1316 | 93.3 | 95.0 | 96.2 | 4.5 |

TABLE IA-continued

COMPARISON OF HYBRIDS 3471 AND 3475 FROM PERIOD OF YEARS RESEARCH DATA

| | | | | | | | | | |
|---|---|---|---|---|---|---|---|---|---|
| DIFF. | 5 | 2 | 3.1 | .0 | 88 | 4.7 | .1 | 3.5 | 2.1 |
| PROB.* | | .00# | .00# | .48 | .00# | .00# | .91 | .00# | .00# |

| | TEST WEIGHT | GRAIN QUALITY | COB SCORE | SEED-LING VIGOR | EARLY STAND COUNT | PLANT HEIGHT | EAR HEIGHT | DROPPED EARS | BRITTLE STALKS |
|---|---|---|---|---|---|---|---|---|---|
| | No. of Reps | | | | | | | | |
| HYBRID | 705 | 484 | 125 | 418 | 612 | 877 | 377 | 558 | 53 |
| 3471 | 56.7 | 6.6 | 6.8 | 6.5 | 59.3 | 19.1 | 3.2 | 99.8 | 96.1 |
| 3475 | 57.8 | 6.7 | 7.3 | 5.8 | 57.7 | 16.7 | 7.1 | 99.7 | 95.9 |
| DIFF. | 1.1 | .2 | .4 | .6 | 1.5 | 2.3 | 1.1 | .1 | .2 |
| PROB.* | .00# | .03+ | .00# | .00# | .00# | .00# | .00# | .05+ | .75 |

*+ and # represent significance at the .05 and .01 probability level, respectively.
Testing Stations: JOHNSTON, IOWA; PRINCETON, ILLINOIS; ALGONA, IOWA; BOWLING GREEN, OHIO; CARROLLTON, MISSOURI; GARDEN CITY, KANSAS; HURON, SOUTH DAKOTA; MARION, IOWA; NEW HOLLAND, PENNSYLVANIA; NORTH PLATTE, NEBRASKA; SHELBYVILLE, ILLINOIS; WINDFALL, INDIANA; YORK, NEBRASKA.

TABLE IB

COMPARISON OF 3471 AND DEKALB PFIZER'S T1100 FROM PERIOD OF YEARS RESEARCH DATA

| | PRE-DICTED RM | SELECTION INDEX | PERCENT YIELD | YIELD (BU./AC.) | MOIS-TURE | GDU SHED | STALK LODG-ING | ROOT LODG-ING | EARS/PLOT |
|---|---|---|---|---|---|---|---|---|---|
| | No. of Reps | | | | | | | | |
| HYBRID | 84 | 84 | 73 | 73 | 74 | 24 | 72 | 12 | 3 |
| 3471 | 113 | 105 | 103 | 162.9 | 20.8 | 1465 | 98 | 76.4 | 92.4 |
| T1100 | 123 | 97 | 101 | 159.9 | 23.2 | 1435 | 77.6 | 75.8 | 83.7 |
| DIFF. | 10 | 8 | 2 | 3 | 2.4 | 30 | 20.4 | .6 | 8.7 |
| PROB.* | | | .34 | .33 | .00# | .00# | .00# | .18 | .11 |

| | STAY GREEN | TEST WEIGHT | GRAIN QUALITY | COB SCORE | SEED-LING VIGOR | EARLY STAND COUNT | PLANT HEIGHT | EAR HEIGHT | DROPPED EARS |
|---|---|---|---|---|---|---|---|---|---|
| | No. of Reps | | | | | | | | |
| HYBRID | 55 | 74 | 69 | 3 | 40 | 64 | 45 | 45 | 45 |
| 3471 | 5.7 | 57.1 | 6.3 | 7.7 | 6.2 | 61.2 | 19.0 | 7.8 | 99.9 |
| T1100 | 3.9 | 55.6 | 5.8 | 5.7 | 5.7 | 57.5 | 17.1 | 6.7 | 99.9 |
| DIFF. | 1.8 | 1.5 | .5 | 2.0 | .5 | 3.8 | 1.9 | 1.1 | 0.0 |
| PROB.* | .00# | .00# | .04+ | .18 | .03+ | .00# | .00# | .00# | .73 |

*+ and # represent significance at the .05 and .01 probability level, respectively.
STATIONS TESTED: BOWLING GREEN, OHIO; NEW HOLLAND, PENNSYLVANIA; WINDFALL, INDIANA; AND YORK, NEBRASKA.

EXAMPLE II

Strip Test Data

Comparison data was collected from strip tests that were grown by farmers. Each hybrid was grown in strips of 4, 6, 8, 12, etc. rows in fields depending on the size of the planter used. The data were collected from strip tests that had the hybrids in the same field. At harvest, the grain was harvested from a measured area and weighed. The moisture percentage was determined to compute yield and bushels per acre was adjusted to 15.5% moisture. Each replication or "rep" represents a distinct field.

Comparison strip testing was done between 3471 and 3475 and between 3471 and DeKalb Pfizer's T1100.

The results are presented in Tables IIA and IIB. Traits characterized on the strip test data in addition to those defined previously are as follows:

Number of Wins. For yield, this number represents the number of times a given hybrid won the comparison. For percent moisture, it would be the number of times a hybrid had lower harvest moisture compared to the other hybrid.

Percent Standing. This is the percentage of plants not broken below the ear at the time of harvest.

Root Lodging. This is based upon a 1-9 rating with 9 representing no lodging and 1 representing a very high level of root lodging.

TABLE IIA

COMPARISON OF HYBRIDS 3471 AND 3475 FROM 1985 STRIP TEST DATA

| | YIELD | | MOISTURE | | | | | | ADJUSTED GROSS INCOME | |
|---|---|---|---|---|---|---|---|---|---|---|
| | BU/AC | NO. OF WINS | % | NO. OF WINS | PERCENT STANDING | ROOT LODGING | PLANTS PER ACRE | TEST WEIGHT | $/AC | NO. OF WINS |
| | NO. OF REPS | | | | | | | | | |
| HYBRID | 201 | | 201 | | 154 | 125 | 159 | 152 | | |
| 3471 | 155.8 | 70 | 20.8 | 118 | 98.0 | 8.8 | 23,600 | 56.3 | 333.88 | 79 |
| 3475 | 160.4 | 128 | 20.9 | 73 | 97.0 | 8.5 | 22,600 | 57.0 | 342.81 | 121 |

DIVISIONS TESTING: ILLINOIS - WISCONSIN, CENTRAL, EASTERN, AND PLAINS

TABLE IIB

COMPARISON OF 3471 AND DEKALB PFIZER'S T1100 FROM 1985 STRIP TEST DATA

| | YIELD | | MOISTURE | | | | | | ADJUSTED GROSS INCOME | |
|---|---|---|---|---|---|---|---|---|---|---|
| | BU/AC | NO. OF WINS | % | NO. OF WINS | PERCENT STANDING | ROOT LODGING | PLANTS PER ACRE | TEST WEIGHT | $/AC | NO. OF WINS |
| | | | | | NO. OF REPS | | | | | |
| HYBRID | 32 | | 32 | | 30 | 28 | 31 | 22 | | |
| 3471 | 164.2 | 17 | 20.0 | 30 | 98.9 | 8.8 | 24,000 | 56.3 | 354.64 | 20 |
| T1100 | 164.8 | 15 | 22.8 | 2 | 94.3 | 7.9 | 23,700 | 54.2 | 346.76 | 12 |

DIVISIONS TESTING: ILLINOIS - WISCONSIN AND EASTERN

EXAMPLE III

Comparison of Key Traits

Characteristics of 3471 were compared to Pioneer brand hybrid 3475 for key traits. Table III gives the comparison characteristics for 3471 compared to Pioneer brand hybrid 3475. These data were compiled utilizing the research data for each of the hybrids that are listed. The ratings given for most of the traits are on a 1 to 9 basis. In these cases 9 would be outstanding, while a 1 would be poor for the given characteristic. The values are based on performance of the given hybrid relative to other Pioneer commercial and precommercial hybrids.

The traits characterized in Table III were defined previously. Disease and insect resistance are rated in Table III. A score of 9 indicates outstanding resistance, while a score of 1 indicates that the hybrid is very susceptible to the disease or insect given. The diseases and insects tested include: anthracnose stalk rot (Anth Stk Rot); northern and southern corn leaf blight (No lf blht and So lf blht); gray leaf spot (gray lf spot); and European corn borer tolerance-second brood (Eur CB2 SC).

TABLE III

CHARACTERISTICS OF 3471 COMPARED TO 3475 FOR KEY TRAITS

| HYBRID | MN RM | BL RM | GDU BL | SLK RM | GDU SLK | MOIST YLD/ | DRY-DOWN | STK LODG | RT LODG | STAY GRN | DROUGHT TOL | TEST WT | PUR SDLG* |
|---|---|---|---|---|---|---|---|---|---|---|---|---|---|
| 3471 | 114 | 119 | 2757 | 119 | 1459 | 7 | 7 | 9 | 7 | 9 | 5 | 4 | 8 |
| 3475 | 114 | 110 | 2658 | 109 | 1382 | 8 | 5 | 5 | 7 | 3 | 8 | 6 | 7 |

| HYBRID | SDLG VIG | DROP EARS | BRITTLE STK | PLANT HT | ANTH STK ROT | NO LF BLHT | SO LF BLHT | EYESPOT | GRAY LF SPOT | HEAD SMUT | EUR CB2 SC |
|---|---|---|---|---|---|---|---|---|---|---|---|
| 3471 | 9 | 5 | 5 | 9 | 5 | 7 | 5 | 5 | — | 4 | 2 |
| 3475 | 4 | 5 | 6 | 3 | 4 | 5 | 5 | 3 | 7 | 3 | 6 |

*9 = Green, 1 = purple.

EXAMPLE IV

Disease and Insect Traits

Table IVA gives the average ratings for disease and insect traits of 3471. Table IVB is a comparison of ratings for disease and insect traits between hybrid 3471 and Pioneer brand hybrid 3475.

TABLE IVA

AVERAGE RATINGS FOR DISEASE AND INSECT TRAITS FOR 3471

| | Corn Lethal Necrosis | Maize Dwarf Mosaic Virus | Anthracnose Stalk Rot | Southern Leaf Blight | Northern Leaf Blight | Helminthosporium Leaf Blight | Common Rust | Gray Leaf Spot | Goss's Wilt |
|---|---|---|---|---|---|---|---|---|---|
| | | | | No. of Locs. | | | | | |
| Hybrid | 1 | 1 | 5 | 1 | 10 | 2 | 1 | 27 | 3 |
| 3471 | 8 | 5 | 5 | 5 | 5 | 8 | 6 | 4 | 4 |

| | Common Smut[1] | Head Smut[1] | Downy Mildew[1] | Fusarium Ear Rot[1] | European Corn Borer I Leaf Feeding | European Corn Borer II Rating | European Corn Borer II[2] Tunnelling | Corn Root Worm Root Lodging Severity |
|---|---|---|---|---|---|---|---|---|
| | | | | | No. of Locs. | | | |
| Hybrid | 3 | 3 | 1 | 3 | 3 | 29 | 1 | 1 |
| 3471 | 95 | 91 | 4 | 50 | 5 | 6 | 7 | 6 |

These ratings are based on a 1 to 9 score with 1 being susceptible and 9 being resistant with the following exceptions:

[1]Percentage not infected. Percentage of plants that did not express symptoms of the disease: Common smut, Head smut, Downy mildew, and Fusarium ear rot.

[2]Length of tunnelling in stalk (inches). This is a measure of the tunnelling in the stalk caused by the insect: European corn borer.

TABLE IVB

| | CLN VIRUS | MDM VIRUS | COMMON SMUT | ANTHRACNOSE STALK ROT | SOUTHERN CORN LEAF BLIGHT | NORTHERN CORN LEAF BLIGHT |
|---|---|---|---|---|---|---|
| | | | No. of Locs. | | | |
| HYBRID | 1 | 1 | 3 | 5 | 1 | 10 |
| 3471 | 8 | 5 | 95 | 5 | 5 | 5 |
| 3475 | 3 | 4 | 94 | 4 | 2 | 4 |

TABLE IVB-continued

| | HELMINTHOSPORIUM LEAF BLIGHT | COMMON RUST | GRAY LEAF SPOT | GOSS'S WILT | HEAD SMUT | DOWNY MILDEW |
|---|---|---|---|---|---|---|
| | No. of Locs. | | | | | |
| HYBRID | 2 | 1 | 20 | 3 | 3 | 1 |
| 3471 | 8 | 6 | 4 | 4 | 91 | 4 |
| 3475 | 5 | 6 | 3 | 8 | 95 | 27 |

EXAMPLE V

Entomology Traits

A comparison was made between the entomology traits of 3471 and Pioneer brand hybrid 3475. The results of this comparison testing is given in Table V.

The following is a brief description of the traits used for these comparisons.

European corn borer, dropped ears. (ECB drop. ear) This is a measure of the number of plants that dropped ears and is an indication of corn borers in the shank. This number is given by a percentage of plants without such dropped ears.

ECB2 SC. This is a visual rating based on degree of second brood corn borer infestation with 9 being resistant.

ECB1 LF. FD. This is a visual rating based on the degree of leaf feeding by first brood corn borer with 9 being resistant.

ECB2 TUN. This is a measure of the total length of corn borer tunnels per plant in inches.

Corn R.W. LDG. This is a visual rating of the amount of root lodging with 9 being no root lodging on plants that have a high level of corn rootworms.

TABLE V

| | ECB Drop. Ear | ECB2 SC | ECB1 Lf. Fd. | ECB2 Tun. | Corn R.W. Ldg. |
|---|---|---|---|---|---|
| | No. of Reps | | | | |
| Hybrids | 4 | 29 | 3 | 1 | 1 |
| 3471 | 100 | 6 | 5 | 7 | 6 |
| 3475 | 98 | 5 | 5 | 12 | 6 |

EXAMPLE VI

Isozyme Genotypes For 3471

Isozyme data was generated for hybrid corn 3471 according to the procedure described in Goodman, M. M. and Stuber, C. M., "Genetic identification of lines and crosses using isoenzyme electrophoresis, "*Proceedings of the Thirty-fifth Annual corn and Sorghum Industry Research Conference*, Chicago, Ill. (1980). The results are shown in the following Table VI.

TABLE VI

ISOZYME GENOTYPES FOR 3471

| Locus | Alleles Present | Frequency |
|---|---|---|
| Acp1 | 3-4 | 50-50 |
| Adh1 | 4 | 100 |
| Cat3 | 9 | 100 |
| Dia1 | 4 | 100 |
| Glu1 | 6-7 | 50-50 |
| Got1 | 4 | 100 |
| Got2 | 2-4 | 50-50 |
| Got3 | 4 | 100 |
| Idh1 | 4 | 100 |
| Idh2 | 6 | 100 |
| Mdh1 | 6 | 100 |
| Mdh2 | 3.5-6 | 50-50 |
| Mdh3 | 16-18 | 50-50 |
| Mdh4 | 12 | 100 |
| Mdh5 | 12 | 100 |
| Pgd1 | 2 | 100 |
| Pgd2 | 5 | 100 |
| Pgm1 | 9 | 100 |
| Pgm2 | 4 | 100 |
| Phi1 | 4 | 100 |

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. Hybrid corn seed designated 3471.

2. A hybrid corn plant and its plant parts produced by the seed of claim 1.

3. Corn plants regenerated from tissue culture of the hybrid corn plant and plant parts of claim 2.

4. A hybrid corn plant with the phenotypic characteristics of the hybrid plant of claim 2.

5. Hybrid seed having ATCC accession no. 40301.

6. A hybrid corn plant with the characteristics of the hybrid seed of claim 5.

* * * * *